United States Patent [19]

Weisz et al.

[11] Patent Number: 5,262,404
[45] Date of Patent: Nov. 16, 1993

[54] CYCLODEXTRIN POLYMERS AND CYCLODEXTRINS IMMOBILIZED ON A SOLID SURFACE

[75] Inventors: Paul B. Weisz, Yardley, Pa.; Yuen W. Shing, Randolph, Mass.

[73] Assignee: The Trustees of the University of Pennsylvania/Childrens Hospital Corporation, Philadelphia, Pa.

[21] Appl. No.: 959,145

[22] Filed: Oct. 9, 1992

Related U.S. Application Data

[63] Continuation of Ser. No. 480,407, Feb. 15, 1990, Pat. No. 5,183,809.

[51] Int. Cl.$^5$ .................. C08B 37/16; A61K 31/71; A61K 31/715
[52] U.S. Cl. ........................... 514/58; 536/103; 536/122
[58] Field of Search ............... 536/103, 122; 514/58

[56] References Cited

U.S. PATENT DOCUMENTS

| | | | |
|---|---|---|---|
| 4,020,160 | 4/1977 | Bernstein et al. | 514/58 |
| 4,247,535 | 1/1981 | Lewis et al. | 536/103 |
| 5,098,793 | 3/1992 | Rohrbach et al. | 536/103 |
| 5,134,127 | 7/1992 | Stella et al. | 536/103 |

OTHER PUBLICATIONS

Croft et al., "Tetrahedron Report Number 147, Synthesis of Chemically Modified Cyclodextrins", *Tetrahedron*, vol. 39, No. 9, pp. 1417 and 1455-1459, (1983).

*Primary Examiner*—Ronald W. Griffin
*Attorney, Agent, or Firm*—Mathews, Woodbridge & Collins

[57] ABSTRACT

Polyionic derivatives of cyclodextrin polymers and cyclodextrins immobilized on a solid surface are disclosed. Compositions and methods for separating a molecular species, including but not limited to a biologically active protein, from a mixture, for the storage of protein factors and for the therapeutic biodelivery of protein factors which employ the polyionic derivatives of cyclodextrin polymers and cyclodextrins immobilized on a solid surface are also disclosed.

7 Claims, 5 Drawing Sheets

CYCLODEXTRIN POLYMERS AND CYCLODEXTRINS IMMOBILIZED ON A SOLID SURFACE

CROSS-REFERENCE

This is a continuation of Ser. No. 07/480,407 filed Feb. 15, 1990, now U.S. Pat. No. 5,183,809.

1. FIELD OF THE INVENTION

The invention is directed to polyionic derivatives of cyclodextrin polymers, and polyionic derivaties of cyclodextrins immobilized on solid surfaces. The invention also relates to compositions and methods for separating molecular species, compositions and methods for the storage of protein factors, and compositions and methods for the biotherapeutic delivery of protein factors. Some embodiments of the invention relate, in particular, to the field of methods of protein purification by affinity chromatography.

2. BACKGROUND OF THE INVENTION

2.1. HEPARIN AND HEPARIN BINDING GROWTH FACTORS

Heparin, a mucopolysaccharide, is a constituent of various tissues, especially liver and lung, and mast cells in several mammalian species. Chemically, it has been described as an $\alpha,\beta$ glycosidically linked sulfated copolymer of D-glucosamine and D-glucuronic acid. It is well known as an anticoagulant that functions by accelerating the rate at which antithrombin III inactivates the proteases of homeostasis (Jacques, 1980, Pharmacol. Rev. 31: 99-166).

The exact structure of heparin and the precise nature by which it acts in blood anticoagulation however has not been discovered. Much of the difficulty in determining the structure of heparin results from its complexity and the fact that it is not a homogeneous, well-defined substance (Barzu et al., 1985, Biochem. Biophys. Acta 845: 196-203; Linhardt et al., 1982, J. Biol. Chem. 257: 7310-7313; Lindahl et al., 1977, Fed. Proc. 36: 19-23; and Laurent et al., 1978, Biochem. J. 175: 691-701). Heparin is also polydisperse with a molecular weight range from about 5,000 to 40,000. Within a given chain, there are also structural variations such as the varying degrees of sulfation, N-acetylation and C-5 epimerization in the uronic acid residue.

Heparin has also been found to coact with cortisone to inhibit angiogenesis (described in U.S. patent application Ser. No. 641,305 filed Aug. 16, 1984, the contents of which are incorporated herein by reference). Angiogenesis is the induction of growth of new capillary blood vessels and is important in normal processes such as development of the embryo, formation of the corpus luteum, and wound healing. It is also an important component in pathological processes such as chronic inflammation, certain immune responses, and neoplasia. Administration of heparin and cortisone to mice with certain kinds of tumors inhibits the generation of essential capillary vessels that support tumor growth, and can cause the collapse of the blood supply which supports the tumors (see Folkman, 1986, Cancer 46: 467 for a review of the history of this discovery and related subject matter).

A major disadvantage in the use of heparin with a steroid to inhibit angiogenesis results from the fact that heparins manufactured by different processes and different companies revealed quite different antiangiogenic activities despite similar anticoagulant activities. The precise composition of commercial heparin apparently varies depending on its source and method of manufacture. This variation could create problems when heparin is used for other purposes.

A number of endothelial cell growth factors, now known as heparin binding growth factors (HBGFs) have been found to have a strong affinity for heparin (reviewed in Lobb, 1988, Eur. J. Clin. Invest. 18: 321-328 and Folkman and Klagsbrun, 1987, Science 235: 442-447). As will be discussed in further detail infra, the purification of HBGFs was greatly facilitated by heparin affinity chromatography. Recently, it has been shown that heparin and the heparin like molecule, hexuronyl hexosaminoglycan sulfate (HHS-4) can protect basic or acidic fibroblast growth factor from acid or heat activation (Gospodarowicz and Cheng, 1986, J. Cell. Phys. 128: 475-484). Heparin has also been found to protect ECGF from proteolytic inactivation.

2.1.1. PURIFICATION OF HBGFS

Affinity chromatography generally involves the use of a solid phase having affinity for a desired component to be separated from contaminating components. The solid phase is contacted with the desired component under conditions in which the two form a complex, and contaminants which form no complex or only a weak complex with the solid phase are readily removed from the solid phase, leaving relatively pure desired component bound to it. The solid phase is then subjected to conditions which cause release of the desired component relatively free of contaminating components.

Heparin affinity chromatography using heparin-Sepharose ® was first used to purify a tumor-derived angiogenic endothelial mitogen in 1984 (Shing et al., 1984, Science 223: 1296-1298). The mitogen was subsequently determined to be basic fibroblast growth factor (bFGF) (Baird et al., 1986, Recent Prog. Horm. Res. 43: 143-205 and Gospodarowicz et al., 1986, Mol. Cell Endocrinol. 46: 187-204). Heparin affinity chromatography has since been widely used for the purification of fibroblast growth factors from a large variety of tissue sources (for reviews see Folkman and Klagsbrun, 1987, Science 235:442-447; Baird et al., 1986, Recent Prog. Horm. Res. 43: 143-205; Gospodarowicz et al., 1986, Mol. Cell. Endocrinol. 46: 187-204; and Lobb et al., 1986, Anal. Biochem. 154: 1-14).

Representative publications describing such use are discussed below.

Klagsbrun U.S. Pat. No. 4,882,275 discloses purification of growth factors by affinity to heparin.

Shing et al., 223 Science 1296 et seq. (1984) describe purification of a tumor-derived capillary endothelial cell growth factor by affinity chromatography, using heparin-Sepharose columns.

D'Amore et al., 99 J. Cell Biology 1545 et seq. (1984) describe the use of heparin-Sepharose columns for growth factors isolated from bovine retina and hypothalamus. Heparin-Sepharose chromatography in conjunction with size-exclusion chromatography reportedly permits rapid 15,000 fold purification of these endothelial cell growth factors.

Maciag et al., 225 Science 932 et seq. (1984) describe purification of endothelial cell growth factors by use of heparin-Sepharose columns.

Conn et al., 124 Biochem. Biophys. Res. Comm. 262 (1984), describe purification to homogeneity of two anionic polypeptides using heparin-affinity chromatography. These polypeptides are growth factors isolated from human brain.

Klagsbrun et al., 82, *Proc. Nat'l. Acad. Sci., USA*, 805 et seq. (1985) describe capillary endothelial (CE) cell growth factors derived from the hypothalamus which adhere tightly to immobilized heparin. They report that:

[a]ffinity for heparin appears to be a property shared by growth factors that are mitogenic for CE cells. All the CE cell growth factors we have tested so far have a marked affinity for heparin. On the other hand PDGF and EGF, which are not mitogenic for CE cells, have very little affinity for heparin. We speculate that the various CE cell growth factors may have in common a structural domain that is involved in binding to heparin.

They further report that their results:
indicate that there is no correlation between heparin-binding and [the net charge of the] growth factor . . .

Sullivan et al., 260 *J. Biol. Chem.* 2399 et seq. (1985) describe purification of cartilidge derived growth factor by heparin affinity chromatography.

Lobb et al., 23 *Biochem.* 6295 et seq. (1984) describe purification of growth factors from bovine neural tissue by heparin affinity chromatography. These growth factors are termed heparin binding growth factors $\alpha$ and $\beta$. See also, Lobb, *Eur. J. Clin. Invest.* 18:321-328 (1987); and Folkman et al. *Science* 235:442-497 (1987); Baird et al. *Recent Prog. Hormone Res.* 43:143-205 (1986); Gospodarowicz et al., *Mol. Cell Endocrinol.* 46:187-204 (1986); Lobb et al., *Anal. Biochem.* 154:1-14 (1986).

Gospodarowicz et al., 81 *Proc. Nat'l. Acad. Sci. USA*, 963 et seq., 1984, describe isolation of brain fibroblast growth factor by heparin-Sepharose ® affinity chromatography; and Gospodarowicz et al., 120 *Biochem. Biophys. Res. Comm.* 554 et seq. (1985) describe purification of fibroblast growth factor from human placenta by use of heparin-Sepharose ® affinity chromatography.

Bohlen et al., 185 *FEBS Letters* 177 (1985) describe purification of human brain fibroblast growth factor by use of heparin-Sepharose ® affinity chromatography.

HBGFs can be subdivided into two classes, typified by basic fibroblast growth factor (bFGF) and acidic fibroblast growth factor (aFGF) on the basis of their isoelectric points and their respective affinities for heparin. bFGF and aFGF exist in multiple molecular weight forms, all of which are heat and acid labile. Therefore, these forms of FGF cannot be isolated by reversed phase high pressure liquid chromatography (HPLC).

Recently, a method was disclosed for separating and identifying the various forms of fibroblast growth factor based on their differential affinities for heparin and copper (Shing, 1988, J. Biol. Chem. 263: 9059-9062). Specifically, FGFs were extracted from bovine hypothalamus and purified by batchwise adsorption to heparin-Sepharose ®. Partially purified FGFs were applied to an affinity column prepared by mixing equal portions of heparin-Sepharose ® and copper Sepharose ®. bFGF was purified 32,052 fold and aFGF was purified 8,131 fold.

2.1.2. FUNCTION AND USES OF HBGFS

HBGFs have been found in a wide variety of normal and malignant tissues and cells (reviewed in Lobb, 1988, Eur. J. Clin. Invest. 18: 321-336). These factors have potent mitogenic effects on endothelial cells. Additionally, HBGFs have been shown to have mitogenic and non-mitogenic effects on virtually all mesoderm and neuroectoderm-derived cells in vitro, and promote the migration, proliferation, and differentiation of these cells in vivo. It was suggested by Lobb (1988, Eur. J. Clin. Invest. 18: 321-328) that HBGFs could therefore effect soft tissue repair, e.g. topical wound healing or nerve regeneration, resulting from injury or degenerative disease. It was also suggested that HBGFs may also be used to effect hard tissue repair, e.g. bone.

2.2. CYCLODEXTRINS

Figure 1A:
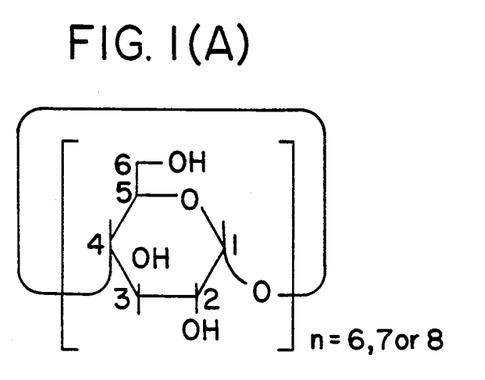

Cyclodextrins (hereinafter referred to for convenience as CD or CDs for the singular and the plural, respectively) are cyclic oligosaccharides consisting of at least six glucopyranose units. Although CDs with up to twelve glucopyranose units are known, only the first three homologs have been studied extensively. These compounds have the simple, well-defined chemical structure shown in FIG. 1(A). The common designations of the lower molecular weight $\alpha$-, $\beta$-and $\gamma$-CDs are used throughout this specification and will refer to the chemical structure shown in FIG. 1(A) wherein n=6, 7, or 8 glucopyranose units, respectively. The initial discovery of the CDs as degradation products of starch was made at about the turn of the century, and Schardinger showed that these compounds could be prepared by the action of *Bacillus macerans* amylase upon starch. In older literature, the compounds are often referred to as Schardinger dextrins. They are also sometimes called cycloamyloses.

Figure 1B:
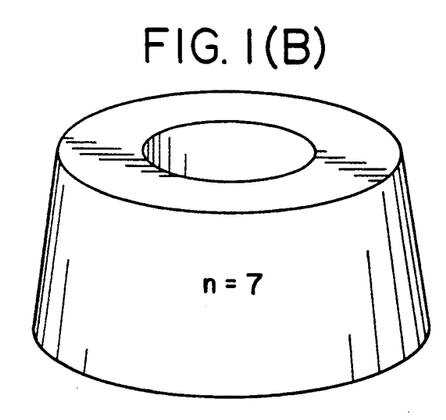

Topographically, the CDs may be represented as a torus, as shown in FIG. 1(B), the upper rim of which is lined with primary —$CH_2OH$ groups, and the lower rim with secondary hydroxyl groups. Coaxially aligned with the torus is a channel-like cavity of about 5, 6 or 7.5 A.U. diameter for the $\alpha$-, $\beta$-, and $\gamma$-CDs, respectively. These cavities make the cyclodextrins capable of forming inclusion compounds with hydrophobic guest molecules of suitable diameters.

A reasonably large number of CD derivatives have been prepared and described in the literature. In general, these chemically modified CDs are formed by reaction of the primary or secondary hydroxyl groups attached to carbons 2, 3 or 6 [FIG. 1(A)], without disturbing the $\alpha$ (1→4) hemiacetal linkages. A review of such preparations is given in "Tetrahedron Report Number 147, Synthesis of Chemically Modified Cyclodextrins", A. P. Croft and R. A. Bartsch, Tetrahedron 39(9):1417-1474 (1983), incorporated herein by reference for background (hereinafter referred to as "Tetrahedron Report No. 147").

In particular, $\alpha$-, $\beta$-, and $\gamma$-CD sulfates (Na salt) are shown as Compound Nos. 207, 208, and 209 in Tetrahedron Report No. 147, (supra) Table 26, p.1456. U.S. Pat. No. 2,923,704 to Berger describes the preparation of cycloamylose sulfates. U.S. Pat. No. 4,020,160 to Berstein et al. and U.S. Pat. Nos. 4,247,535 and 4,258,180 to Lewis et al. disclose the use of modified cyclodextrin sulfates as complement inhibitors. U.S. Pat. No. 4,383,992 to Lipari describes the preparation of a water-soluble inclusion compound of a steroid and unmodified $\beta$-cyclodextrin. U.S. Pat. No. 4,596,795 to Pitha discloses the administration (by the sublingual or buccal route) of sex hormones, particularly testosterone, progesterone and estradiol in the form of their inclusion compounds with hydroxypropyl-$\beta$-CD or poly-$\beta$-CD.

None of the foregoing references are believed to show or make obvious applicants, invention as described and claimed herein.

2.2.1. CYCLODEXTRIN POLYMERS

Cyclodextrin polymers have been produced by linking or cross-linking cyclodextrins or mixtures of cyclodextrins and other carbohydrates with polymerizing agents, e.g. epichlorhydrin, diizocynanates, diepoxides (Insoluble cyclodextrin polymer beads, Chem. Abstr. No. 222444m, 102: 94; Zsadon and Fenyvesi, 1st. Int. Symp. on Cyclodextrins, J. Szejtli, ed., D. Reidel Publishing Co., Boston, pp. 327-336; Fenyvesi et al., 1979, Ann. Univ. Budapest, Section Chim. 15: 13 22; and Wiedenhof et al., 1969, Die Stirke 21: 119-123). These polymerizing agents are capable of reacting with the primary and secondary hydroxy groups on carbons 6, 2, and 3. Polymerization will not eliminate the central cavity of cyclodextrin molecules. Stable water soluble cyclodextrin polymers may be formed by linking two to five cyclodextrin units. (Fenyvesi et al. 1st Int. Symp. on Cyclodextrins, J. Szejtli, ed., D. Reider Publishing Co., Boston, p. 345).

Insoluble cyclodextrin polymers can be prepared in the form of beads, fiber, resin or film by cross-linking a large number of cyclodextrin monomers as described in the previous paragraph, supra. Such polymers have the ability to swell in water. The characteristics of the polymeric product, chemical composition, swelling and particle size distribution may be controlled by varying the conditions of preparation. These cyclodextrin polymers have been shown to be used as a stationary phase in the chromatographic separation of aromatic compounds and aliphatic amino acids from one another (Harada et al., 1982, Chem. Abstr. No. 218351u, 96:10 and Zsadon and Fenyvesi, 1982, 1st. Int. Symp. on Cyclodextrins, J. Szejtli, ed., D. Reidel Publishing Co., Boston, pp. 327-336). Additionally, beta-cyclodextrin immobilized with epichlorohydrin has been used as a catalyst for the selective synthesis of 4-hydroxybenzaldehyde (Komiyama and Hirai, 1986, Polymer J. 18: 375-377).

2.2.2. CYCLODEXTRINS IMMOBILIZED ON SOLID SURFACES

Immobilized cyclodextrins may be obtained using a variety of procedures. One method involves linking vinyl derivatives of cyclodextrin monomers. For example, water soluble polymers containing cyclodextrin have been obtained using acrylic ester derivatives (Harada et al., 1976, J. Am. Chem. Soc. 9: 701-704).

Immobilized cyclodextrins have also been obtained by covalently linking cyclodextrin to a solid surface via a linker arm, or by incorporating them into synthetic polymer matrices by physical methods (Zsadon and Fenyvesi, 1982, 1st. Int. Symp. on Cyclodextrins, J. Szejtli, ed., D. Reidel Publishing Co., Boston, pp. 327-336). Cyclodextrin monomers have been attached to silica gel through silanes (Armstrong et al., 1987, Science 232:1132 and Armstrong U.S. Pat. No. 4,539,399) and by reacting carboxylated silica with ethylenediamine monosubstituted cyclodextrin (Kawaguchi et al., 1983, Anal. Chem., 55: 1852-1857). Cyclodextrin has also been covalently linked to polyurethane resins (Kawaguchi et al., 1982, Bull. Chem. Soc. Jpn. 55: 2611-2614), Sepharose ®, BioGel ®, cellulose (Zsadon and Fenyvesi, 1982, 1st Int. Symp. on Cyclodextrins, J. Szejtli, ed., D. Reidel Publishing Co., Boston, pp. 327-336). Such cyclodextrin containing solid surfaces have been used as stationary phases in the chromatographic separation of aromatic compounds (Kawaguchi et al., 1983, Anal. Chem., 55: 1852-1857). Additionally cyclodextrin has been linked to polyacrylamide (Tanaka, 1982, J. Chromatog. 246:207-214 and Tanaka et al., 1981, Anal. Let. 14:281-290).

3. SUMMARY OF THE INVENTION

The invention is directed to a polyionic derivative of a cyclodextrin polymer. The invention is also directed to a polyionic derivative of at least one cyclodextrin immobilized on a solid surface. Polyionic derivatives of a cyclodextrin polymer and at least one cyclodextrin immobilized on a solid surface may be used to separate molecular species and to store protein factors.

The invention further provides compositions comprising (1) a polyionic derivative of a cyclodextrin polymer in combination with (2) a metal ion capable of being monovalent or divalent, in which the metal ion is immobilized on a solid surface or; compositions comprising (1) a polyionic derivative of at least one cyclodextrin immobilized on a solid surface, in combination with (2) a metal ion capable of being monovalent or divalent immobilized on a solid surface. These compositions may be used to separate molecular species.

A polyionic derivative of a cyclodextrin polymer or a polyionic derivative of at least one cyclodextrin immobilized on a solid surface may also be used to stabilize protein factors. The invention relates to methods for stabilizing such protein factors which comprise contacting the protein factor with an effective amount of a polyionic derivative of a cyclodextrin polymer or a polyionic derivative of at least one cyclodextrin immobilized on a solid surface. This invention also relates to the resulting compositions comprising: (1) a polyionic derivative of a cyclodextrin polymer in combination with (2) the protein factor; or alternatively (1) a polyionic derivative of at least one cyclodextrin immobilized on a solid surface in combination with (2) the protein factor.

The invention further provides compositions and methods for the therapeutic biodelivery of a protein factor. In one embodiment, the composition comprises (1) a polyionic derivative of at least one cyclodextrin in combination with (2) a biocompatible porous solid. In another embodiment, a polyionic derivative of a cyclodextrin polymer may be used for the therapeutic biodelivery of a protein factor.

The invention further provides a method for separating a desired protein (as used herein, the term "protein" is intended to encompass both small and large polypeptides) from a crude mixture. The method includes the following steps. First, a solid phase having a polyionic derivatized cyclodextrin is provided. The polyionic derivative of cyclodextrin may be anionic, e.g., sulfated or phosphorylated; or the polyionic derivative of cyclodextrin may be cationic, e.g., a quaternized amine. Next, the solid phase is contacted with the mixture under conditions in which the desired protein binds strongly to the polyionic derivatized cyclodextrin, but contaminating substances do not bind to the polyionic derivatized cyclodextrin (or bind with sufficiently weaker adhesive force that they can be removed without removing the desired protein). The method also includes removing the unbound contaminating substances from the solid phase, while the desired biologically active protein remains bound to that solid phase, and then contacting the solid phase with a solution which causes the desired protein to be removed from the derivatized cyclodextrin into the solution.

4. BRIEF DESCRIPTION OF THE FIGURES

The present invention may be more fully understood by reference to the following detailed description of the invention, examples of specific embodiments of the invention and appended figures in which:

FIG. 1 (A and B) is a schematic representation of: (A) the chemical structure of alpha-, beta-, and gamma-cyclodextrins; and (B) of the three dimensional shape of these cyclodextrins.

5. DETAILED DESCRIPTION OF THE INVENTION

The invention is directed to a polyionic derivative of a cyclodextrin polymer or a polyionic derivative of at least one cyclodextrin immobilized on a solid surface. The invention is also directed to compositions and methods for separating a molecular species, including but not limited to a protein, from a crude mixture using a polyionic derivative of a cyclodextrin polymer or a polyionic derivative of at least one cyclodextrin immobilized on a solid surface in combination with a metal ion capable of being monovalent or divalent immobilized on a solid surface. In one embodiment, the invention encompasses compositions and methods for separating a protein having biological activity in a mammal, for example, a human, from a crude mixture.

The invention is further directed to compositions and methods for the storage of a protein factor using a polyionic derivative of a cyclodextrin polymer or a polyionic derivative of at least one cyclodextrin immobilized on a solid surface. The invention also relates to compositions and methods for the therapeutic biodelivery of a protein factor comprising a polyionic derivative of at least one cyclodextrin in combination with a biocompatible porous solid or a polyionic derivative of a cyclodextrin polymer.

5.1. POLYIONIC DERIVATIVES OF CYCLODEXTRIN POLYMERS

The invention is directed to a polyionic derivative of an alpha-, beta-, or gamma-cyclodextrin polymer. In a most preferred embodiment, a polyionic derivative of a cyclodextrin polymer may be prepared by first linking cyclodextrin monomers chemically via polymerizing agents, e.g. epichlorohydrins, diisocyanates, diepoxides, silanes using procedures known in the art to form a cyclodextrin polymer (see Section 2.2.1., supra). Alternatively a cyclodextrin polymer may be obtained from commercial sources. A cyclodextrin polymer may be obtained in forms including but not limited to beads, fiber, resin or film. The cyclodextrin polymer is then derivatized with ionic substituents.

The polyionic derivative of alpha-, beta-, or gamma-cyclodextrin may be a cationic or anionic derivative. An example of a cationic derivative of alpha-, beta-, or gamma cyclodextrin polymer is an alpha-, beta-, or gamma cyclodextrin quarternized amine polymer.

An anionic derivative of alpha-, beta-, or gamma-cyclodextrin may contain an anionic group selected from the group consisting of sulfate, phosphate, carboxylate, nitrate, and mixtures thereof. The derivatives useful herein will exhibit electrolytic conductivity and osmotic properties characteristic of electrolytes and polyelectrolytes when in aqueous solution. A preferred derivative would be an alpha-, beta-, or gamma-cyclodextrin polymer containing about 10–16 sulfate groups per cyclodextrin monomer. A particularly preferred derivative is beta-cyclodextrin tetradecasulfate polymer.

5.2. POLYIONIC DERIVATIVES OF CYCLODEXTRIN IMMOBILIZED ON A SOLID SURFACE

The invention is directed to polyionic derivatives of at least one alpha-, beta-, or gamma-cyclodextrin immobilized on a solid surface. The polyionic derivative of alpha-, beta-, or gamma-cyclodextrin may be cationic or anionic. Examples of such cationic and anionic moieties or groups are disclosed in Section 5.1., supra. A polyionic derivative of at least one cyclodextrin immobilized on a solid surface can be prepared by (1) immobilizing at least one cyclodextrin on a solid surface then derivatizing the immobilized cyclodextrin with an ionic substituent or (2) derivatizing a cyclodextrin with an ionic substituent, and then immobilizing the derivatized cyclodextrin onto a solid surface. Such solid surfaces include but are not limited to silica gel, alumina, controlled pore glass, agarose materials such as Sepharose ®, which is a beaded gel form of agarose, cellulose, polyurethane, and polyacrylamide. In a preferred embodiment, a sufficient number of cyclodextrin molecules are immobilized on the solid surface so that a substantial portion of the surface area of the solid surface is covered with cyclodextrin molecules. The surface area of the solid surface may be determined using methods known in the art such as BET measurements.

Polyionic derivatives of at least one alpha-, beta-, or gamma-cyclodextrin can be immobilized on a solid surface in one embodiment by covalently linking the cyclodextrin to the solid surface via a linker arm using procedures known in the art, then derivating the immobilized cyclodextrin with an ionic substituent. Alternatively, cyclodextrins covalently linked to a solid surface can be obtained from commercial sources. A method of covalent coupling to a versatile polymer is illustrated by the following example. Polystyrene polymers are manufactured in a great variety of structural forms, i.e. with various pore size openings (specific surface area) and degrees of rigidity to swelling (via different degrees of cross-linking). An example of such polymer linkages are the Amberlysts produced by Rohm and Haas. In the process of creating cation exchangers from these structures, a common intermediate is the polystyrene polymer structure with chloromethyl groups on the constituent benzene rings, which offer the reactive sites for further chemical derivatization. These groups lend themselves to reaction with hydroxyl groups of cyclodextrins, by available chemical reaction techniques. Thus, the cyclodextrin-derivatized polystyrene polymer can then be sulfated at the sites of the remaining hydroxyl groups of the cyclodextrin substituents.

In another embodiment, cyclodextrin can be polymerized by bonding to a solid substance such as polyacrylamide or polyurethane to form a copolymer. See generally, Tanaka, 1982, J. Chromatog. 246:207–214; Tanaka et al., 1981, Anal. Lett. 14:291–290 (polyacrylamide); and Mizobuchi et al., 1980, J. Chromatog. 194:153; 1981, J. Chromatog. 208:35 and 1981, J. Chromatog. 219:109 (polyurethane).

In still another embodiment, polyanionic cyclodextrins can be impregnated on an inorganic oxide which strongly binds anions, such as alumina, in particular beta-alumina, gamma-alumina, and alpha-alumina. This procedure consists of contacting the oxide with a solution containing the polyanionic cyclodextrin for a sufficient time to approach complete or a sufficient degree of adsorption. Preferably, such contact is followed by drying and heating at temperatures below the decomposition temperature of the cyclodextrin, preferably at about 60° to 130° C.

In yet another embodiment, polyionic derivatives of at least one alpha-, beta-, or gamma-cyclodextrin may be immobilized on a solid surface via electrostatic interactions between the ionic entities of the solid surface. The cyclodextrin would first be derivatized with an ionic substituent then immobilized on a solid surface.

In a further embodiment, cyclodextrin may be joined to a magnetic carrier (e.g. magnetite) by cross-linking the cyclodextrin to the carrier. The cyclodextrin is subsequently derivatized with ionic substituents and may be retained on the solid surface by a magnetic field.

Polyionic derivatives of a least one alpha-, beta-, or gamma-cyclodextrin may also be immobilized on a biocompatible porous solid. The phrase "biocompatible porous solid" as used herein means a solid which may be applied or administered to a mammal without provoking an inflammatory response or other adverse effects. Such biocompatible porous solids include but are not limited to membranes such as collagen-based polymeric membranes, amniotic membranes, and omentum membranes (reviewed in Cobb, 1988, Eur. J. Clin. Investig. 18:321–326). Polyionic derivatives of cyclodextrins may be immobilized on such membranes in a preferred embodiment by contacting polyionic cyclodextrins with electrostatic binding partners on the membrane. Biocompatible porous solids may also include but are not limited to ethylene vinyl acetate and methylcellulose polymers, silicone rubber, polyurethane rubber, polyvinyl chloride, polymethylacrylate, polyhydroxyethyl methylacrylate, polyethylene terephthalate, polypropylene, polyterafluorethylene, polyethylene, polyfluoroethlene, propylene, cellulose acetate, cellulose, and polyvinyl alcohol (reviewed in Hoffman, Synthetic Polymeric Biomaterials in "Polymeric Materials and Artificial Organs" ACS Symposium Series #256, (G. Gebelein, ed.) 1988). In a preferred embodiment, the cyclodextrin would be coupled with reactive groups contained in the polymer at some stage of manufacture, such as amine, amide, carboxylate end groups, etc. and then subsequently derivatived with ionic substituents.

5.3. COMPOSITIONS AND METHODS FOR THE SEPARATION OF MOLECULAR SPECIES

The invention is further directed to compositions and methods for separating a molecular species from contaminating substances or from a crude mixture. As used herein, the term "molecular species" includes but is not limited to polyionic dyes, cationic or polyionic salts of chemical complexes including organic and/or inorganic compounds, and proteins. According to one embodiment, the compositions and methods are useful to separate a biologically active protein from a mixture. According to a preferred embodiment, the biologically active protein exhibits a specific affinity for heparin, and, more specifically, is a heparin-binding growth factor, e.g., growth factors which are mitogenic for endothelial cells. An example of such a growth factor is fibroblast growth factor. Other proteins which can be purified using the methods and compositions of the invention include complement, anti-thrombin III, fibronectin, lipoprotein lipase, platelet factor IV, hyaluronidase, and RNA polymerase as well as the proteins listed in Table I.

To determine whether a protein is a candidate for purification by the methods of the invention, one can determine whether it has a specific affinity for heparin or a derivatized cyclodextrin—i.e., whether it will remain substantially bound to one of those substances (e.g., using a derivatized column) while a liquid having relatively low salt concentration is in contact with this solid phase. Generally, at least 80% of such bound protein will remain attached under such conditions. Contaminating proteins having little or no specific affinity for the substance. (even those with a pI similar to the desired protein) will be substantially, for example, at least 90%, removed from contact with the substance under these conditions. As explained in further detail in Klagsbrun U.S. Pat. No. 4,882,275, it will be appreciated that overall affinity of the protein for a substance such as cyclodextrin is a combination of both non-specific charge-related effects and specific affinity. Cationic growth factors will bind more strongly to anionic cyclodextrin derivative (which generally has a non-specific charge-related affinity for positively charged species) and will require a higher ionic strength to cause elution. Anionic growth factors can also bind strongly to anionic cylcodextrin (particularly to sulfated cyclodextrin).

TABLE I

| PROTEIN FACTORS | | |
|---|---|---|
| Symbol | Name | Reference |
| IL-1 | (Interleukin-1) | Henderson & Pettipher, 1988, Biochem. Pharmacol. 37:4171; Endo et al., 1988, BBRC 136:1007, Hopkins et al., 1988, Clin. Exp. Immunol. 72:422 |
| IL-2 | (Interleukin-2) | Weil-Hillman et al., 1988, J. Biol. Response Mod. 7:424; Gemlo et al., 1988, Cancer Res. 48:5864 |
| IFNα | (Interferon α) | Pitha et al., 1988, J. Immunol. 141:3611; Mangini et al., 1988, Blood 72:1553 |
| IFNγ | (Interferon γ) | Blanchard & Djeu. 1988, J. Immunol. 141:4067; Cleveland et al., 1988, J. Immunol. 141:3823 |
| TNFα | (Tumor necrosis factor α) | Plate et al., 1988, Ann. NY . Acad. Sci. 532:149; Hopkins & Meager, 1988, Clin. Exp. Immunol. 73:88; Granger et al. 1988, J. Biol. Response Med. 7:488 |
| EGF | (Epidermal growth factor) | Carpenter and Cohen, 1979, A. Rev. Biochem, 48:193–216 |
| FGF | (Fibroblast growth factor, acidic and | Folkman and Klagsburn, 1987, Science 235:442–447 |

TABLE I-continued
PROTEIN FACTORS

| Symbol | Name | Reference |
| --- | --- | --- |
| IGF-1 | basic)<br>(Insulin-like growth factor-1) | Blundell and Humbel, 1980, Nature 287:781-787; Schoenle et al., Nature 296:252-253 |
| IFG-2 | (Insulin-like growth factor-2) | Blundell and Humbel, supra. |
| PDGF | (Platelet-derived growth factor) | Ross et al., 2986, Cell 46:155-169; Richardson et al., 1988, Cell 53:309-319 |
| TGF-α | (Transforming growth factor-α) | Derynck, 1988, Cell 54:593-595 |
| TGF-β | (Transforming growth factor-β) | Cheifetz et al., 1987, Cell 48:409-416 |

The compositions may be used to separate two of the same class of molecular species form one another, e.g. separate two different dyes from one another. Alternatively, the compositions may be used to separated two different classes of molecular species from one another, e.g. a cationic compound from a non-cationic compound.

The composition comprises a polyionic derivative of an alpha-, beta-, or gamma-cyclodextrin polymer or a polyionic derivative of at least one cyclodextrin immobilized on a solid surface. Such derivatives are described in section 5.1 and 5.2, supra.

In another embodiment, the composition comprises (1) a polyionic derivatives of an alpha-, beta-, or gamma-cyclodextrin polymer disclosed in section 5.2, supra, in combination with (2) a metal ion capable of being univalent or divalent immobilized on a solid surface. These include but are not limited to copper, palladium, platinum, and indium. In yet another embodiment, the composition comprises (1) a polyionic derivative of at least one alpha-, beta-, or gamma-cyclodextrin immobilized on a solid surface in combination with (2) a metal ion capable of being univalent or divalent immobilized on a solid surface. These compositions are prepared using procedures known in the art. Cyclodextrin and the metal ion can be immobilized on a solid surface using the procedure described in Section 5.2 supra, e.g. via covalent linkage of the cyclodextrin to the solid surface followed by ionic substitution, electrostatic interactions between an ionic solid surface and a polyionic cyclodextrin or impregnation. Such solid surfaces include but are not limited to silica gel, alumina controlled pore glass, agarose, cellulose, materials such as Sepharose ®, polyurethane, and polyacrylamide.

A molecular species may be separated from contaminating substances using the compositions of the present invention by contacting a solution containing the molecular species with the polyionic derivative of a cyclodextrin polymer, or a polyionic derivative of at least one cyclodextrin immobilized on a solid surface alone or in combination with a metal ion capable of being univalent or divalent immobilized on a solid surface under conditions in which the molecular species binds strongly to the cyclodextrin but contaminating substances do not bind or at most bind only weakly to the cyclodextrin. The contaminating substances are removed from contact with the solid phase, while the molecular species remains bound to the cyclodextrin. The molecular species bound to the polyionic derivative of a cyclodextrin polymer or immobilized cyclodextrin is subsequently contacted with a solution which causes the desired molecular species to be removed from the cyclodextrin into the solution.

In one particular embodiment, the method of purifying includes providing a solid phase having a second substance having affinity for the biologically active protein, for example, a metal ion which is capable of being monovalent or divalent, such as a copper ion. Such biaffinity systems permit separation of the desired protein from contaminants that would otherwise co-elute with the desired protein from the cyclodextrin derivative.

In another particular embodiment, elution is accomplished by a solution of successively increasing molar strength of an electrolyte or salt, as for example, sodium chloride. The increase can be accomplished in one or more steps or continuously. The latter procedure is known as gradient elution. In this manner, the protein components of higher sorptive capacity are recovered by and can be separated and recovered from the solution in later eluant fractions. As a particular single example, substances having little affinity for cyclodextrin derivative are removed from contact with cyclodextrin derivative by a solution that is no more than 0.5 molar with respect to sodium chloride, whereas those having strong affinity for cyclodextrin derivative could remain bound (at lest 90%) to the cyclodextrin derivative under those conditions.

Finally, cyclodextrin can be joined to a magnetic carrier (e.g. magnetite), by cross-linking the cyclodextrin to the carrier. The cyclodextrin may be retained in the reaction column by a magnetic field.

Generally, the solid phase comprising derivatized cyclodextrin is used to contact a mixture of materials to be separated. The cyclodextrin derivative is thereafter separated from the contact fluid, resulting in an enrichment of a bioactive component on the cyclodextrin derivative, and a corresponding removal of the bioactive component from the fluid. As described above, the cyclodextrin derivative complex can be chromatographically separated from the fluid; or a highly charged cyclodextrin complex can be drawn electrically into a separate phase, or through a membrane into a separate fluid by electro-dialysis. Alternatively, the separation may be achieved by addition of suitable solvent to produce a phase separation of the cyclodextrin derivative. For example, addition of a suitable solvent will result in crystallization or precipitation of the cyclodextrin derivative complex, which is then physically separated from the fluid. Other methods are also useful.

Other methodology suitable for separation of bioactive components in this invention includes combining the derivatized cyclodextrin with a magnetic carrier particle, for use in magnetically stabilized bed technology. Here, solid particles are moved counter-current to the flow of fluid without losing integrity of the bed, i.e., without particle mixing. This allows continuous chromatography with devices of relatively small dimensions compared to conventional apparatus for purification chromatography. Magnetite is an example of a magnetic carrier. The joining of the derivatized cyclodextrin and the magnetic component can be achieved by various methods, e.g., cross-linking of cyclodextrin with surface groups of magnetite ($Fe_2O_4$), and subsequent chemical addition of sulfates or other groups; combining an anionic derivatized cyclodextrin salt with cation-containing iron, or other magnetic salt, preferably having bi- or poly-valent cations; co-precipitating an iron oxide, or other magnetic metal oxide (usually as hydroxide), together with silicate ion to form a silica/metal oxide gel, and then binding derivatized cyclodextrin; chemical coupling cyclodextrin to the magnetic carrier, followed by chemical conversion of cyclodextrin to derivatized cyclodextrin; and generating a magnetic sol, gel, or other precipitate containing or entrapping a derivatized cyclodextrin or a cyclodextrin, which is then chemically converted to derivatized cyclodextrin.

Continuous separation is achieved by use of derivatized cyclodextrin-containing solids suspended in a magnetically stabilized bed. These solids are allowed to move through a fixed column design, counter-current to fluid containing the agents to be separated. At specified locations electrolytes are added to modify the composition of the flowing liquid, thereby altering the elution properties along the axis of the column.

5.4. COMPOSITIONS AND METHODS OF STORAGE OF PROTEIN FACTORS

A polyionic derivative of an alpha-, beta-, or gamma cyclodextrin polymer or a polyionic derivative of at least one cyclodextrin immobilized on a solid surface may be used to store protein factors by contacting the protein with an effective amount of a polyionic derivative of a cyclodextrin polymer (described in Section 5.1. supra) or an effective amount of at least one cyclodextrin immobilized on a solid surface (described in Section 5.2, supra) resulting in the formation of a protein factor/polyionic derivative of a cyclodextrin polymer complex, hereinafter referred to as a protein/cyclodextrin polymer complex or a protein factor/polyionic derivative of at least one cyclodextrin immobilized on a solid surface hereinafter referred to as a protein factor/cyclodextrin complex. Such protein factors include but are not limited to heparin binding growth factors (e.g. fibroblast growth factor, brain endothelial cell growth factor, retina-derived growth factor) and the protein factors listed on Table I, supra.

The protein factor may be bound to the cyclodextrin by contacting the protein factor suspended in a solution such as a low salt solution that promotes the binding of the protein factor to the cyclodextrin. The protein factor may be released by contacting the protein factor/cyclodextrin polymer or protein factor/cyclodextrin complex with a such or a solution such as a high salt solution that would promote the release of the protein factor

5.5. COMPOSITIONS AND METHODS FOR THE THERAPEUTIC BIODELIVERY OF PROTEIN FACTORS

The invention additionally relates to compositions and methods for the therapeutic biodelivery of protein factors. Such protein factors include but are not limited to heparin binding growth factors (e.g. fibroblast growth factor, brain endothelial cell growth factor, retina derived growth factor), and the factors listed in Table I, supra. As described in Section 2.1.2., supra, heparin binding growth factors could be used to effect soft and hard tissue repair resulting from injury or disease. The potential uses for interferons, interleukins, and tissue growth factors are well known in the art.

The compositions comprise (1) a polyionic derivative of at least one alpha-, beta-, or gamma-cyclodextrin disclosed in Section 5.1. supra in combination with (2) a biocompatible porous solid, examples of which are disclosed in section 5.2. supra. Alternatively, the compositions may comprise polyionic derivatives of cyclodextrin polymers. Such polymers may be in the form of, for example, beads, fiber, resin or film.

The invention also relates to methods for the administration of an effective amount of a protein factor in combination with a polyionic derivative of at least one cyclodextrin immobilized on a biocompatible porous solid, or a polyionic derivative of a cyclodextrin polymer. Such methods include but are not limited to grafting or implantating the compositions on the area to be treated with effective amounts of the composition. Alternatively, the compositions, where cyclodextrin polymers are used, may be administered, for example, intraperitaneally, orally, intralesionally, subcutaneously, parenterally or the like.

6. EXAMPLE: USE OF BETA CYCLODEXTRIN TETRADECASULFATE POLYMER FOR AFFINITY CHROMATOGRAPHY PURIFICATION OF FIBROBLAST GROWTH FACTOR

In the example described herein, beta-cyclodextrin tetradecasulfate polymer was found to have a strong affinity for fibroblast growth factor (FGF) and demonstrated to be advantageously useful for FGF purification. Basic FGF was purified about 200,000 fold from a rat chondrosarcoma extract using a method of biaffinity chromatography in which beta-cyclodextrin tetradecasulfate polymer was mixed with copper-Sepharose ®.

6.1. MATERIALS AND METHODS

6.1.1. PREPARATION OF GROWTH FACTORS

Human recombinant basic fibroblast growth factor (bFGF) was provided by Takeda Chemical Industries, Ltd. It was purified from *E. coli* as previously described (Kurokawa et al., 1987, FEBS. Letters 213: 189-194 and Iwane et al., 1987, Biochem. Biophys. Res. Commun. 146: 470-477).

Rat chondrosarcoma-derived growth factor (ChDGF) was isolated from the transplantable tumor as previously described (Shing et al. 1984, Science 223: 1296-1298). One hundred ml of the crude extract prepared by collagenase digestion of the tumor was diluted (1:1) with 0.6M NaCl in 10 mM Tris, pH 7 and loaded directly onto a heparin-Sepharose ® column (1.5×9 cm) pre-equilibrated with the same buffer. The column was rinsed with 100 ml of 0.6M NaCl in 10 mM Tris, pH 7. ChDGF was subsequently eluted with 18 ml of 2M NaCl in 10 mM Tris, pH 7.

6.1.2. PREPARATION OF SULFATED BETA-CYCLODEXTRIN POLYMER

Beta-cyclodextrin polymer beads (American Maize Products) of 20-60 mesh particle size were derivatized to form a novel immobilized CD polymer sulfate derivative according to the present invention. The composition approaches a degree of sulfation of nearly two sulfates per glucose ring of the CD polymer. 0.4 g of carefully dried polymer were reacted with 1.7 g of trimethylammonium sulfur trioxide complex (Aldrich) in 100 ml of dried dimethylformamide (DMF), with mild agitation at 62° to 72° C. for 3 to 4 days. The solids were washed in DMF, reacted with 30% aqueous sodium acetate for 24 hours, and washed and stored in distilled water. The sulfur content of the product was 14.7 wt. %. This compares favorably to the value of 17.5% if the polymer mass were composed 100% of β-cyclodextrin tetradecasulfate without cross-linking components, and all glucose hydroxyl units were sterically available (which cannot be expected for the polymer).

6.1.3. BETA-CYCLODEXTRIN AFFINITY CHROMATOGRAPHY OF FGF

The insoluble sulfated beta-cyclodextrin polymer (0.5 ml bed volume), was incubated with 0.5 ml of 0.1M NaCl, 10 mM Tris, pH 7 containing 1,000 units of human recombinant bFGF at 4° C. for 1 hour with mixing. Subsequently, the polymer was rinsed stepwise with 2 ml each of 0.1, 0.6, and 2M NaCl in 10 mM Tris, pH 7. All fractions eluted from the polymer were assayed for growth factor activity.

6.1.4. BETA-CYCLODEXTRIN-COPPER BIAFFINITY CHROMATOGRAPHY

The beta-cyclodextrin-copper biaffinity column was prepared by mixing 0.5 ml each of the sulfated beta-cyclodextrin polymer and chelating Sepharose (Pharmacia) that had been saturated with copper (II) chloride. A sample (16 ml) of Chondrosarcoma-derived growth factor partially purified by batchwise adsorption to heparin-Sepharose ® was applied directly to this biaffinity column (1×1.3 cm) pre-equilibrated with 2M NaCl, 10 mM Tris, pH 7. The column was rinsed consecutively with 40 ml each of the following four reagents in 10 mM Tris, pH 7: (i) 2M NaCl, (ii) 0.6M NaCl, (iii) 0.6M NaCl plus 10 mM imidazole, and (iv) 0.6M NaCl. Finally, the growth factor was eluted at a flow rate of 20 ml/hour with a linear NaCl/imidazole gradient from 100 mM imidazole in 10 mM Tris, pH 7. Fractions (4 ml) were collected, monitored for conductivity (Radiometer American conductivity meter) and assayed for growth factor activity.

6 1.5. GROWTH FACTOR ASSAY

Growth factor activity was assessed by measuring the incorporation of [$^3$H]thymidine into the DNA of quiescent, confluent monolayers of BALB/c mouse 3T3 cells in 96-well plates. One unit of activity was defined as the amount of growth factor required to stimulate half-maximal DNA synthesis in 3T3 cells (about 10,000 cells/0.25 ml of growth medium/well). For determination of specific activities, protein concentrations of the crude extract and the active fraction eluted from heparin-Sepharose column were determined by the method of Lowry et al. (1952, J. Biol. Chem. 193:265-275). Protein concentrations of the pure growth factor were estimated by comparing the intensities of silver-stained polypeptide bands of SDS-polyacrylamide gel to those of the molecular weight markers.

6.2 RESULTS

6.2.1. AFFINITY OF FIBROBLAST GROWTH FACTOR FOR BETA CYCLODEXTRIN TETRADECASULFATE POLYMER

Figure 2:
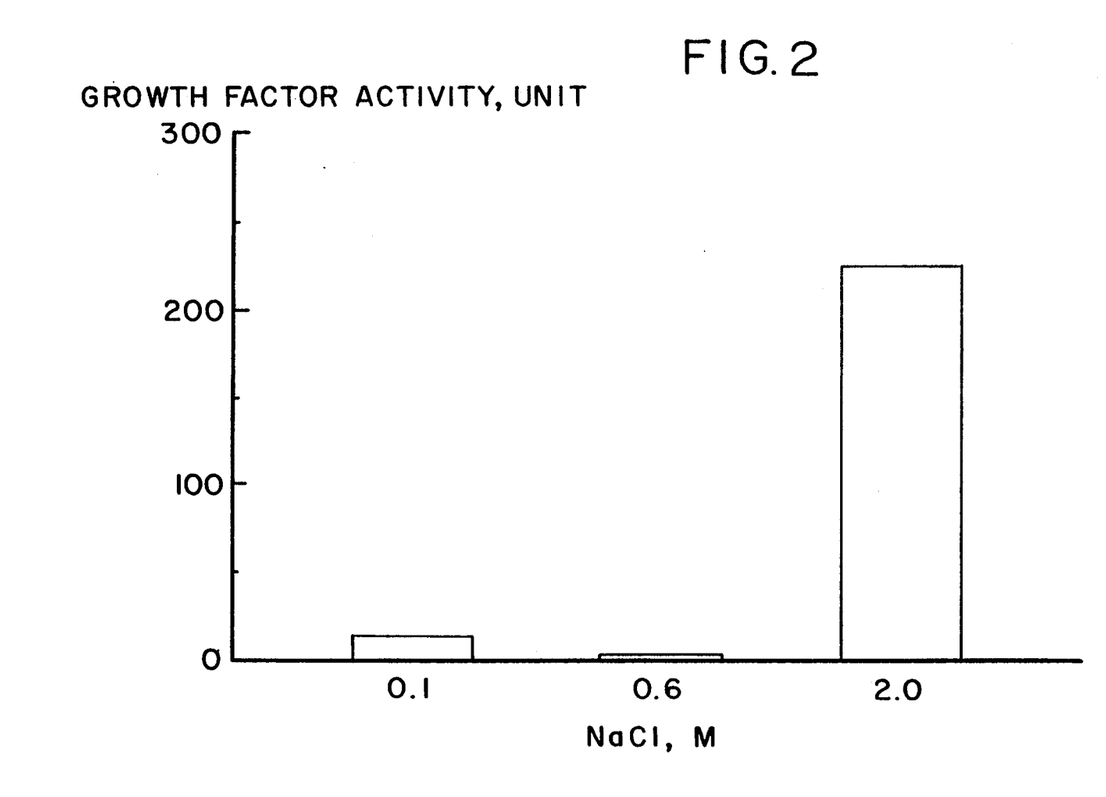
FIG. 2 shows the affinity of beta-cyclodextrin tetradecasulfate sulfate polymer for basic fibroblast growth factor.

Human recombinant bFGF (1000 units) was incubated with sulfated beta-cyclodextrin polymer. The polymer was subsequently eluted stepwise with 0.1M, 0.6M, and 2M NaCl. The results are shown in FIG. 2.

While most of the growth factor activity remained bound to the polymer at 0.6M NaCl, approximately 230 units of the activity was recovered when eluted with 2M NaCl. These results indicate that basic fibroblast growth factor has a very strong affinity for beta-cyclodextrin tetradecasulfate and is at least comparable to that of FGF for heparin. The activity peak was analyzed by SDS polyacrylamide gel electrophoresis followed by a silver stain.

Figure 3:
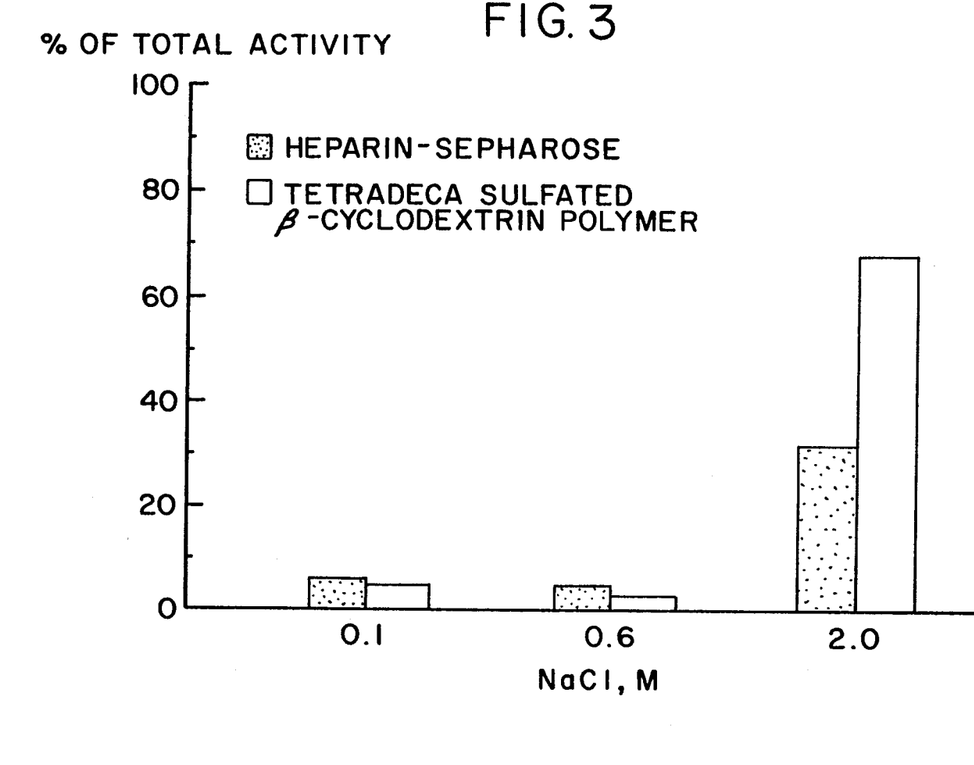
FIG. 3 compares the affinities of heparin and beta-cyclodextrin tetradecasulfate polymer for Chondrosarcoma-derived growth factor.

The affinities of heparin and beta-cyclodextrin tetradecasulfate for chondrosarcoma derived growth factor were also tested. Chondrosarcoma extracts which contained about 500 units of growth factor activity were incubated individually with heparin-Sepharose ® and beta-cyclodextrin tetradecasulfate polymer. The beads were subsequently eluted stepwise with 0.1M, 0.6M, and 2M NaCl. The results are shown in FIG. 3. Approximately 32% and 68% of the total activity was recovered at 2M NaCl with heparin Sepharose ® and beta cyclodextrin tetradecasulfate polymer, respectively.

6.2.2. BETA-CYCLODEXTRIN TETRADECASULFATE POLYMER COPPER BIAFFINITY CHROMATOGRAPHY

Samples of chondrosarcoma extract, partially purified by heparin Sepharose ® were loaded directly onto a beta-cyclodextrin tetradecasulfate copper biaffinity column. After appropriate rinses, the growth factor was eluted with a linear NaCl/imidazole gradient. Aliquots of the eluates were assayed for mitogenic activity and monitored for conductivities, which were plotted by equivalent concentrations of NaCl.

Figure 4:
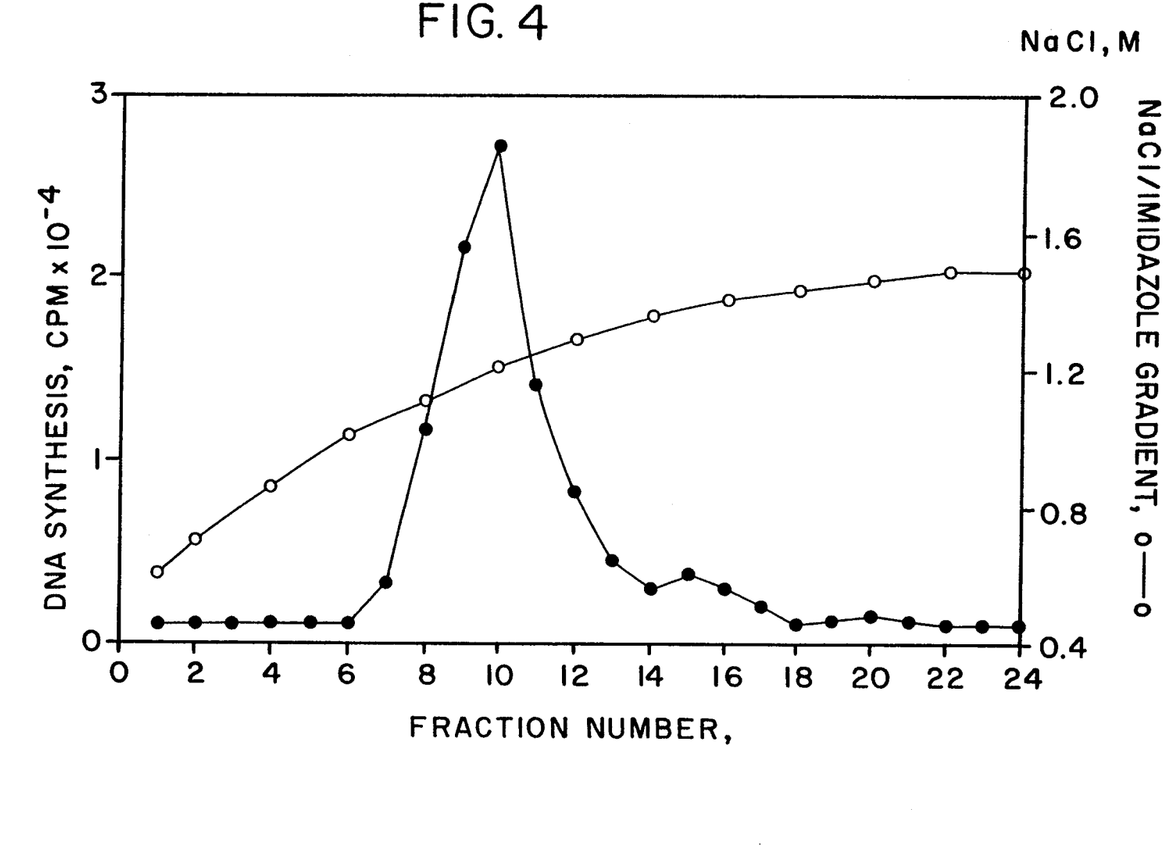
FIG. 4 illustrates cyclodextrin-copper biaffinity chromatography of Chondrosarcoma extract.
Figure 5:
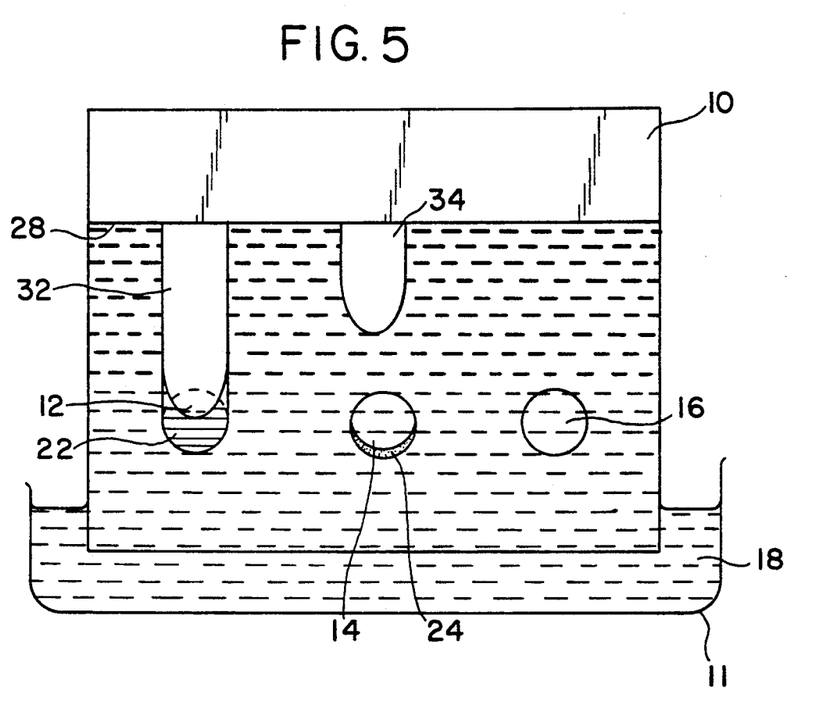
FIG. 5 depicts the relative migration of a substance applied to a alumina TLC plate immobilized with cyclodextrin sulfate.

The results are shown in FIG. 4 and Table II. A peak of growth factor activity was identified at about 1.2M NaCl and 4.3 mM imidazole. Analysis of the eluates from the activity peak (fractions 9 to 11) were analyzed by SDS gel electrophoresis followed by a silver stain. Lane 3 in FIG. 5 shows that pure Chondrosarcoma-derived growth factor was obtained.

As shown in Table II, a 207,000 fold purification was obtained. This is considerably higher than what was obtained by others when heparin-copper biaffinity chromatography was used to resolve multiple forms of FGF (Shing, 1988, J. Biol. Chem. 263: 9059).

TABLE II

| Purification of Chondrosarcoma-Derived Growth Factor | | | | |
|---|---|---|---|---|
| Purification Step | Total Activity µg | Total Activity units | Specific Activity units/µg | Activity Recovery % | Purification fold |
| Crude extract | 786,000 | 5,600 | 0.0071 | 100 | — |
| Heparin adsorption | 2,300 | 832 | 0.36 | 14.8 | 51 |
| Sulfated cyclodextrin-copper biaffinity chromatography | 0.5 | 736 | 1,472 | 13 | 207,000 |

7. EXAMPLE: IMMOBILIZATION OF CYCLODEXTRIN SULFATE ON ALUMINA PLATES

In the example described herein, cyclodextrin tetradecasulfate was immobilized on alumina. The ability of the immobilized cyclodextrin tetradecasulfate to adsorb various dyes is disclosed.

Referring to FIG. 5, a (1 µL) droplet, 12, of solution containing 0.8 g/l of sulfated beta-CD (tetradecasulfate) was placed on a thin-layer chromatography (TLC) plate of alumina (Uniplate Alumina G precoated TLC plate, Alaltech, Newark, Del.) 10, and allowed to dry for at least 10 minutes at 60° C. A partially sulfated CD, 14, and a non-sulfated CD, 16, were similarly immobilized.

When plate 10 is allowed to contact a solution, 18, of the cationic dye Alcian Blue 8GX (Aldrich, Lot BV 05821AV) 18 at 0.5 g/l in 0.25M acetate buffer in a suitable container 11, the front of the solution migrates towards and past test spots 12, 14 and 16. The spot of immobilized sulfated CD 12 is intensely dyed shown at 22 as a result of strong adsorption of the dye. The progression solution leaves a "white shadow", 32, behind the impregnated spot as a result of exhaustive depletion of dye molecules from that portion of the solution 28 (otherwise light blue), which continues to migrate beyond spot 12.

With non-sulfated CD, no staining of the dried spot of CD 16 occurs, and no "white shadow" or any alteration of color of the migrating solution is seen. A partially sulfated CD 14, similarly immobilized and tested, produces only a little staining 24 and a relatively short "white shadow" 34.

This binding phenomenon of highly sulfated immobilized cyclodextrin is resistant to high concentrations of electrolyte as shown in tests of the above type, when increasing amounts of magnesium chloride are added to the dye solution. As shown in Table III, the staining strength of cyclodextrin tetradecasulfate (CD-14S) is maintained up to nearly 1.0 molar strength of the electrolyte. Also, when the equivalent experiment was repeated with herapin, it is seen that the staining property of the CD-14S in fact resembles that of heparin. It should be noted that, in fact, Alcain Blue staining in the presence of electrolyte is a method known in histology to detect the presence of highly sulfated glycosaminoglycans, specifically heparins, immobilized by tissues (Scott and Dorling, 1965, Histochemie 5, 221; Dorling, 1969, J. Med. Lab. Technol. 26, 124–130; Snow et al., Human Pathology, 18, 506–510, 1987; Snow, Tillmer and Kisilevsky, 1987, Lab. Invest. 56 (1), 120–123).

TABLE III

| Sample (mg/ml) | TLC Stain Test (Alcian Blue - pH 5.6) $MgCl_2$ - conc. (M) | | | |
|---|---|---|---|---|
| | 0 | 0.6 | 1.0 | 1.2 |
| Heparin (0.8) | ++ | ++ | + | − |
| CD (0.8) | − | − | − | − |
| CD-14S (0.8) | ++ | ++ | + | − |
| CD-7S (4.0) | − | − | − | − |

It is significant to see this similarity between cyclodextrin and heparin in the physical chemistry of interaction with polyanionic dyes, as well as in cell biology (histological behavior, angiogenic behavior on endothelium). However, cyclodextrin is not a complex glycosaminoglycan like heparin, but a relatively simple molecule, reproducibly synthesized by simple and few steps of synthesis. The latter has not been possible for heparin.

It is further significant that our sulfated cyclodextrin polymer will also sorb and bind polycationic dyes such as Alcian Blue and others. The specific nature of sorption of the polycationic dye Alcian Blue by CD-sulfate is demonstrated by the fact that another dye, phenolphthalein, is adsorbed by non-derivatized cyclodextrin, and this phenomenon has been used to devise a quantitative method for determining the presence of cyclodextrin (see M. Vikmon, "Rapid and Simple Spectrophotometric Method for Determination of Micro-amounts of Cyclodextrins"). However, the sulfated CD derivative will not adsorb this dye, thus demonstrating an exactly opposite behavior. A $3 \times 10^{-5}$M solution of phenolphthalein solution (with $4 \times 10^{-3}$M sodium carbonate) is visibly bleached by the presence of 50 $\mu$M beta-cyclodextrin; but no effect at all was seen by the presence of 5000 $\mu$M of beta-cyclodextrin tetradecasulfate.

It is thus seen that the immobilized CD-sulfates are capable of binding, and thereby removing or separating a variety of molecules, which include proteins and other polycationic organic molecules.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A process for the preparation of polysulfated polymer of an alpha-, beta-, or gamma-cyclodextrin which comprises subjecting a solid, water insoluble polymer of an alpha-, beta-, or gamma-cyclodextrine to sulfating conditions until the degree of sulfation is from about 10 to about 16 sulfate groups per cyclodextrin unit of the polymer.

2. The process according to claim 1 in which the degree of sulfation is about 14 sulfate groups per cyclodextrin unit of the polymer.

3. A process for the preparation of polysulfated alpha-, beta-, or gamma-cyclodextrin immobilized on a solid surface which comprises subjecting a solid, water insoluble composition of an alpha-, beta-, or gamma-cyclodextrin immobilized on a solid surface to sulfating conditions until the degree of sulfation is from about 10 to about 16 sulfate groups per immobilized cyclodextrin unit.

4. The process according to claim 3 in which the alpha, beta, or gamma-cyclodextrin monomer is immobilized on a solid surface selected from the group consisting of silica gel, alumina, controlled pore glass, agarose, cellulose, and polyurethane.

5. The process according to claim 4 in which the solid surface is a bead-formed gel of agarose.

6. The process according to claim 4 in which the solid surface is a porous polymeric biocompatible solid.

7. The process according to claim 6 in which the polymeric biocompatible porous solid is selected from the group consisting of collagen based polymeric membrane, amniotic membrane, omentum membrane, ethylene vinyl acetate methylcellulose polymer, silicone rubber, polyurethane rubber, polyvinyl chloride, polymethylacrylate, polyhydroxyethyl methylacrylate, polyethylene terephthalate, polypropylene, polytetrafluoroethylene, polyethylene, polyfluoroethylene, propylene, cellulose acetate, cellulose, and polyvinyl alcohol.

* * * * *